US00PP19396P2

(12) United States Plant Patent
Bunker

(10) Patent No.: US PP19,396 P2
(45) Date of Patent: Oct. 28, 2008

(54) ***CHRYSOCEPHALUM* PLANT NAMED 'FLOCHRORA'**

(50) Latin Name: *Chrysocephalum apiculatum*
Varietal Denomination: Flochrora

(75) Inventor: Kerry Veianne Bunker, Redland Bay (AU)

(73) Assignee: Floreta Pty. Ltd., Queensland (AU)

( * ) Notice: Subject to any disclaimer, the term of this patent is extended or adjusted under 35 U.S.C. 154(b) by 11 days.

(21) Appl. No.: 11/800,798

(22) Filed: May 7, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Chrysocephalum* plant named 'Flochrora', characterized by its compact and outwardly spreading plant habit; freely flowering habit; inflorescences with yellow to orange-colored disc florets; upright to pendulous flowering stems; and long flowering period.

1 Drawing Sheet

Botanical designation: *Chrysocephalum apiculatum.*
Cultivar denomination: 'Flochrora'.

BACKGROUND OF THE INVENTION

The present invention relates to a new and distinct cultivar of *Chrysocephalum* plant, botanically known as *Chrysocephalum apiculatum,* and hereinafter referred to by the name 'Flochrora'.

The new *Chrysocephalum* is a product of a planned breeding program conducted by the Inventor in Redland Bay, Queensland, Australia. The objective of the breeding program is to create new compact and long-flowering *Chrysocephalum* cultivars with numerous and attractive flowers.

The new *Chrysocephalum* originated from a cross-pollination made by the Inventor in Redland Bay, Queensland, Australia in 2000, of a proprietary selection of *Chrysocephalum apiculatum* identified as code number 02-036, not patented, as the female, or seed, parent with a proprietary selection of *Chrysocephalum apiculatum* identified as code number 02-037, not patented, as the male, or pollen, parent. The new *Chrysocephalum* was discovered and selected by the Inventor as a single flowering plant from within the progeny of the stated cross-pollination grown in a controlled environment in Redland Bay, Queensland, Australia in 2001.

Asexual reproduction of the new *Chrysocephalum* by vegetative cuttings in a controlled environment in Redland Bay, Queensland, Australia since 2002, has shown that the unique features of this new *Chrysocephalum* are stable and reproduced true to type in successive generations.

SUMMARY OF THE INVENTION

The cultivar Flochrora has not been observed under all possible environmental conditions. The phenotype may vary somewhat with variations in environment such as temperature and light intensity, without, however, any variance in genotype.

The following traits have been repeatedly observed and are determined to be the unique characteristics of 'Flochrora'. These characteristics in combination distinguish 'Flochrora' as a new and distinct cultivar of *Chrysocephalum:*

1. Compact and outwardly spreading plant habit.
2. Freely flowering habit.
3. Inflorescences with yellow to orange-colored disc florets.
4. Upright to pendulous flowering stems.
5. Long flowering period.

Plants of the new *Chrysocephalum* differ from plants of the female parent selection in the following characteristics:

1. Plants of the new *Chrysocephalum* and the female parent selection differ in leaf shape.
2. Plants of the new *Chrysocephalum* are more freely flowering than plants of the female parent selection.
3. Plants of the new *Chrysocephalum* have longer peduncles than plants of the female parent selection.

Plants of the new *Chrysocephalum* differ from plants of the male parent selection in the following characteristics:

1. Plants of the new *Chrysocephalum* have narrower leaves than plants of the male parent selection.
2. Plants of the new *Chrysocephalum* are more freely flowering than plants of the male parent selection.
3. Plants of the new *Chrysocephalum* have longer peduncles than plants of the male parent selection.

Plants of the new *Chrysocephalum* can be compared to plants of the *Chrysocephalum* cultivar Baby Gold, not patented. In side-by-side comparisons conducted in Redland Bay, Queensland, Australia, plants of the new *Chrysocephalum* differed from plants of the cultivar Baby Gold in the following characteristics:

1. Plants of the new *Chrysocephalum* had broader leaves than plants of the cultivar Baby Gold.
2. Plants of the new *Chrysocephalum* and the cultivar Baby Gold differed in leaf color.
3. Plants of the new *Chrysocephalum* were more freely flowering than plants of the cultivar Baby Gold.

BRIEF DESCRIPTION OF THE PHOTOGRAPHS

The accompanying photographs illustrate the overall appearance of the new *Chrysocephalum.* These photographs show the colors as true as it is reasonably possible to obtain in colored reproductions of this type. Colors in the photographs may differ slightly from the color values cited in the detailed botanical description which accurately describe the colors of the new *Chrysocephalum*.

The photograph at the bottom of the sheet comprises a side perspective view of a typical flowering plant of 'Flochrora' grown in a container.

The photograph at the top of the sheet is a close-up view of typical inflorescences of 'Flochrora'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bonsall, Calif. during the summer in an outdoor nursery and under conditions and practices which approximate those generally used in commercial *Chrysocephalum* production. During the production of the plants, day temperatures ranged from about 18° C. to 38° C. and night temperatures ranged from about 16° C. to 24° C. Measurements and numerical values represent averages for typical flowering plants. Plants were about nine weeks old when the photographs and description were taken.

Botanical classification: *Chrysocephalum apiculatum* cultivar Flochrora.

Parentage:

*Female, or seed, parent.*—Proprietary selection of *Chrysocephalum apiculatum* identified as code number 02-036, not patented.

*Male, or pollen, parent.*—Proprietary selection of *Chrysocephalum apiculatum* identified as code number 02-037, not patented.

Propagation:

*Type.*—By vegetative cuttings.

*Time to initiate roots, summer.*—About one week at 30° C.

*Time to initiate roots, winter.*—About two weeks at 20° C.

*Time to produce a rooted young plant, summer.*—About three weeks at 30° C.

*Time to produce a rooted young plant, winter.*—About four weeks at 20° C.

*Root description.*—Fine to fibrous; pale brown in color.

*Rooting habit.*—Freely branching; moderately dense.

Plant description:

*Plant form/growth habit.*—Compact and outwardly spreading plant habit; open plant form; flowering stems upright to pendulous. Vigorous growth habit. Freely branching habit with about seven lateral branches per plant with numerous secondary and tertiary branches.

*Plant height.*—About 29 cm.

*Plant diameter or spread.*—About 46 cm.

*Lateral branches.*—Length: About 28 cm. Diameter: About 2 mm. Internode length: About 2 cm. Aspect: Upright to outwardly spreading or pendulous. Strength: Moderately strong; flexible. Texture: Pubescent. Color: 148B.

Foliage description:

*Arrangement.*—Alternate; simple.

*Length.*—About 2.5 cm.

*Width.*—About 9 mm.

*Shape.*—Spatulate.

*Apex.*—Cuspidate.

*Base.*—Attenuate.

*Margin.*—Entire.

*Texture, upper and lower surfaces.*—Pubescent.

*Venation pattern.*—Pinnate; arcuate.

*Color.*—Developing foliage, upper surface: 144A. Developing foliage, lower surface: 148C. Fully expanded foliage, upper surface: 146A; venation, 147B. Fully expanded foliage, lower surface: 148B; venation, 148B.

*Petiole length.*—About 9 mm.

*Petiole diameter.*—About 2 mm.

*Petiole texture, upper and lower surfaces.*—Pubescent.

*Petiole color, upper surface.*—Close to 147A.

*Petiole color, lower surface.*—Close to 147B.

Inflorescence description:

*Appearance.*—Composite inflorescence form without ray florets; inflorescences rounded, hemispherical. Inflorescences positioned above and beyond the foliage on erect to pendulous peduncles. Inflorescences face upright to outward. Freely flowering habit; about 90 inflorescences and inflorescence buds per lateral branch. Inflorescences persistent. Inflorescences faintly fragrant, straw-like.

*Time to flower.*—Under mild weather conditions, plants will flower year-round in Southern California. Inflorescences last about seven to ten days on the plant.

*Inflorescence bud.*—Height: About 4 mm. Diameter: About 4 mm. Shape: Rounded. Color: 14A.

*Inflorescence size.*—Diameter: About 6 mm. Depth (height): About 7 mm. Disc diameter: About 5 mm. Receptacle diameter: About 6 mm. Receptacle height: About 4 mm.

*Ray florets.*—Ray floret development has not been observed.

*Disc florets.*—Shape: Tubular; apex dentate and reflexed. Length: About 4 mm. Diameter: Less than 1 mm. Number of disc florets per inflorescence: About 220. Color, immature: Apex: Close to 13A. Mid-section: Close to 1B. Base: Close to 145D. Color, mature: Apex: Close to 21A. Mid-section: Close to 1B. Base: Close to 145D.

*Phyllaries.*—Quantity per inflorescence: About 100 arranged in about eight to nine whorls. Length: About 4 mm. Width: About 1.5 mm. Shape: Lanceolate. Apex: Acute. Base: Truncate. Margin: Entire. Texture, upper and lower surfaces: Pubescent. Color, upper surface: Close to 13A. Color, lower surface: Close to 12B.

*Peduncles.*—Length: About 3 mm to 8 mm. Diameter: About 1 mm. Strength: Moderately strong; flexible. Aspect: About 15° to 30° from the flowering stem axis. Texture: Pubescent. Color: Close to 196B.

*Reproductive organs.*—Androecium: Quantity per disc floret: Five. Anther shape: Oblong. Anther length: About 1 mm. Anther color: Close to 163A. Filament length: About 2 mm. Filament color: Close to 145D. Pollen amount: None observed. Gynoecium: Quantity per disc floret: One. Pistil length: About 4 mm. Stigma shape: Rounded. Stigma color: Close to 163A. Style length: About 2 mm. Style color: Close to 194C. Ovary color: Close to 157D.

*Seed/fruit.*—Seed and fruit development have not been observed.

Disease/pest resistance: Plants of the new *Chrysocephalum* have not been shown to be resistant to pathogens and pests common to *Chrysocephalum*.

Garden performance: Plants of the new *Clematis* have exhibited good tolerance to rain and wind and have been observed to tolerate temperatures from about −4° C. to about 40° C.

It is claimed:

1. A new and distinct *Chrysocephalum* plant named 'Flochrora' as illustrated and described.

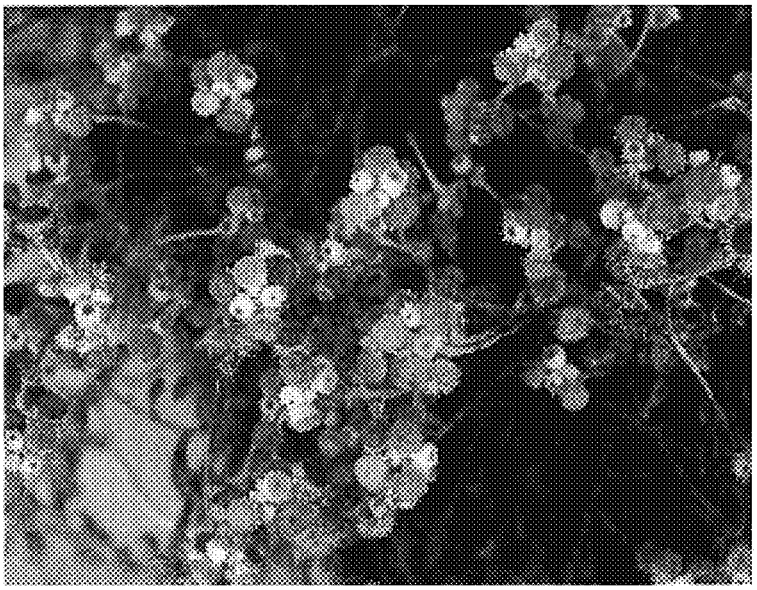
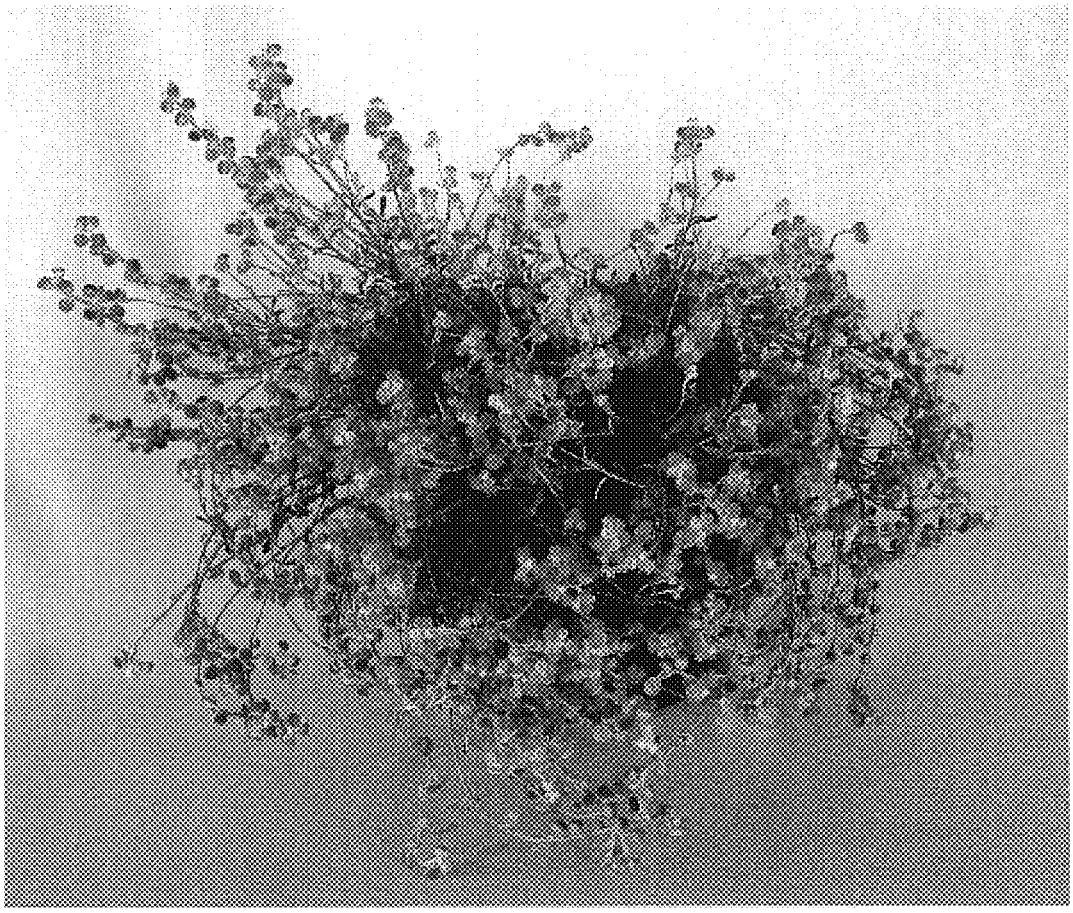

* * * * *